United States Patent [19]

Nobel

[11] Patent Number: 5,430,183
[45] Date of Patent: Jul. 4, 1995

[54] PARA-HYDROXYALKYLATION OF HYDROXYLATED AROMATIC COMPOUNDS

[75] Inventor: Dominique Nobel, Fontaines/Saint/Martin, France

[73] Assignee: Rhone-Poulenc Chimie, Courbevoie Cedex, France

[21] Appl. No.: 89,308

[22] Filed: Jul. 12, 1993

[30] Foreign Application Priority Data

Jul. 10, 1992 [FR] France ................. 92 08578

[51] Int. Cl.$^6$ ............................................. C07C 65/01
[52] U.S. Cl. ................................................ 562/478
[58] Field of Search ...................................... 562/478

[56] References Cited

U.S. PATENT DOCUMENTS 4,329,497  5/1982  Kaniss et al. ............... 562/478

OTHER PUBLICATIONS

Patent Abstracts of Japan, vol. 12, No. 491 (C-554)(3338) 21 Dec. 1988, & JP-A-63 203 631 (Nippon Kayaku Co. Ltd.) Aug. 23, 1988.

*Primary Examiner*—Paul J. Killos
*Attorney, Agent, or Firm*—Burns, Doane, Swecker & Mathis

[57] ABSTRACT

Hydroxylated aromatic compounds devoid of substituents in the para-position to the hydroxyl group thereof are para-hydroxyalkylated, e.g., into optionally substituted p-hydroxymandelic acid compounds, more particularly p-hydroxymandelic acid and 3-methoxy-p-hydroxymandelic acid, by condensing same with an organic carbonyl compound in the presence of a quaternary ammonium hydroxide.

20 Claims, No Drawings

PARA-HYDROXYALKYLATION OF HYDROXYLATED AROMATIC COMPOUNDS

BACKGROUND OF THE INVENTION

1. Field of the Invention

The present invention relates to the para-hydroxyalkylation of hydroxylated aromatic compounds, and, more especially, to the preparation of optionally substituted, p-hydroxymandelic compounds, more particularly the preparation of p-hydroxymandelic acid and 3-methoxy-p-hydroxymandelic acid.

By the term "hydroxylated aromatic compound," as utilized herein, is intended any aromatic compound bearing at least one hydroxyl substituent and the para-position of which being free or devoid of any substituents. By the term "optionally substituted, p-hydroxymandelic compound" is intended an aromatic compound at least bearing a —CHOH—COOH substituent in the para-position to a hydroxyl group.

2. Description of the Prior Art

One of the standard syntheses for the preparation of p-hydroxymandelic acids entails conducting a condensation, in an alkaline medium, of glyoxylic acid with phenol and/or its corresponding derivatives. The yield is limited by the fact that the condensation reaction is not selective and also produces o-hydroxymandelic acids and dimandelic acids.

In addition, the reaction yield is reduced as a result of a parasitic or competing secondary reaction. Thus, glyoxylic acid in an aqueous alkaline medium is transformed, via the Cannizaro reaction, into oxalic and glycolic acids. To prevent this Cannizaro reaction from preponderating and consuming the glyoxylic acid, FR-A-2,132,364 describes carrying out the condensation reaction in a diluted aqueous medium and at low or ambient temperature.

To improve the regio-selectivity of the reaction, EP-A-368,696 describes conducting the condensation of the glyoxylic acid with phenol in the presence of an amine. The amine is a tertiary amine which is liquid at ambient temperature and insoluble in water, such as, e.g., tributyl amine, trioctyl amine, triisooctyl amine or mixtures thereof. One of the disadvantages of this process is that the yields are not satisfactory, and range from 70% to 74%. Moreover, the phenol/glyoxylic acid molar ratio is very high, which mandates the recycling of a significant amount of phenol. Finally, another drawback to this process is that the reaction is carried out in a two-phase medium, requiring the separation of the aqueous and organic phases.

SUMMARY OF THE INVENTION

Accordingly, a major object of the present invention is the provision of a novel process for the preparation of an optionally substituted, p-hydroxymandelic compound via the para-hydroxyalkylation of a hydroxylated aromatic compound.

Briefly, the present invention features a process for the para-hydroxyalkylation of a hydroxylated aromatic compound, the para-position to the hydroxyl group being free, comprising condensing, in the presence of a quaternary ammonium hydroxide, (1) a hydroxylated aromatic compound having the general formula (I):

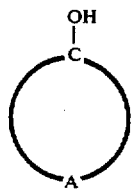

in which A is the residue of an aromatic carbocycle having at least 5 atoms in the optionally substituted, monocyclic or polycyclic ring member, said compound of formula (I) being substituted by at least one hydroxyl group and the para-position of the hydroxyl group being free, with (2) a carbonyl compound having the general formula (II):

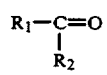

in which $R_1$ is a hydrogen atom, a straight or branched alkyl radical having from 1 to 6 carbon atoms or a phenyl radical, and $R_2$ is an electron-attracting group.

DETAILED DESCRIPTION OF PREFERRED EMBODIMENTS OF THE INVENTION

More particularly according to the present invention, it has now been determined that use of a quaternary ammonium hydroxide in lieu of an alkali metal hydroxide increases the selectivity of the subject process. Another advantage of the process according to the invention is that the reaction can be carried out in an aqueous medium, in the absence of any organic solvent.

By the term "electron-attracting group" is intended a moiety as defined by H. C. Brown in the text, Jerry March, *Advanced Organic Chemistry*, chapter 9, pp. 243/4.

Exemplary electron-attracting groups suitable for the present invention include:

a —CHO group;

a $R_3$—CO— or $R_3$—CO—$(CH_2)_m$ group, in which $R_3$ is a straight or branched alkyl radical having from 1 to carbon atoms and m is a number ranging from 1 to 3;

a —COOR$_4$ group, in which R$_4$ is a hydrogen atom or a straight or branched alkyl radical having from 1 to 6 carbon atoms;

a —CX$_2$H group, in which X is a halogen atom, preferably a fluorine, chlorine or bromine atom;

a —CX$_3$ group, in which X is a halogen atom and preferably a fluorine, chlorine or bromine atom.

Exemplary carbonyl compounds having the formula (II) include:

glyoxal,
glyoxylic acid,
chloral, bromal, fluoral,
dichloroacetone,
trifluoroacetone,
trifluoroacetophenone,
trifluoroacetylacetone,
methyl pyruvate and ethyl pyruvate.

Among the aforesaid carbonyl compounds, glyoxylic acid is the preferred.

The process according to the invention is particularly applicable to phenol, and also to substituted phenols having at least one unsubstituted para-position.

The aromatic nucleus bears at least one hydroxyl group, but it can also bear one or more other substituents. Generally, the term "other substituents" connotes less than four substituents per aromatic nucleus. Any substituent can be present, provided that it does not interfere with the reaction according to the invention.

Thus, the process according to the invention is applicable to hydroxylated aromatic compounds having the following formula (I):

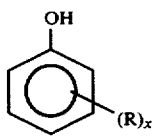

in which the position para to the hydroxyl group is unsubstituted, or free, x is an integer ranging from 1 to 4, and R is a hydrogen atom, a group having from 1 to 20 carbon atoms selected from among alkyl, alkoxy, hydroxyalkyl, cycloalkyl, aryl, phenoxy, alkoxyalkyl, fluoroalkyl and hydroxyalkoxyalkylene groups, a hydroxyl group, a —CHO group, an acyl group having from 2 to 6 carbon atoms, a halogen atom, preferably a fluorine, chlorine or bromine atom, with the proviso that two R groups depending from adjacent carbon atoms may together form, with said adjacent carbon atoms from which they depend, a benzene nucleus.

Exemplary of the radicals R which can be borne by the aromatic nucleus are:

Alkyl radicals such as methyl, ethyl, propyl, isopropyl, butyl, isobutyl, sec. butyl, tert. butyl, n-octyl, 2-ethyl, hexyl, decyl, octadecyl and eicosyl radicals;

Alkoxy radicals such as methoxy, ethoxy, propoxy, isopropoxy, butoxy, hexyloxy, decyloxy, hexadecyloxy, octadecyloxy and phenoxy radicals;

Hydroxyalkyl radicals such as hydroxymethyl, hydroxyethyl, hydroxypropyl, hydroxyhexyl and hydroxydecyl radicals;

Cycloalkyl radicals such as cyclopentyl, cyclohexyl and cycloheptyl radicals;

Fluoroalkyl radicals such as fluoromethyl, difluoromethyl, trifluoromethyl, fluoroethyl, 1,1,1-trifluoroethyl, pentafluoroethyl, fluoropropyl, fluorobutyl and trifluoroamyl radicals;

Hydroxyalkoxyalkylene radicals such as hydroxymethyloxyethylene, hydroxyethyl-di-(oxyethylene), hydroxyethyl-tri-(oxyethylene), hydroxyethyloxy-1,2-propylene, hydroxyethyloxybutylene, hydroxypropyloxypropylene, hydroxybutyloxybutylene and hydroxybutyl-di-(oxybutylene) radicals;

Halogen atoms such as fluorine, chlorine, bromine and iodine.

The preferred hydroxylated aromatic compounds having the general formula (I) are those in which x is equal to 0, 1, 2 or 3; and R is a hydrogen atom, a straight or branched alkyl radical having from 1 to 10 carbon atoms and preferably 1 to 4 carbon atoms, a straight or branched alkoxy radical having from 1 to 10 carbon atoms, preferably 1 to 4 carbon atoms, a —OH group, a —CHO group, a halogen atom, or a —CF$_3$ group. Even more preferred compounds of formula (I) are those in which the R radicals, which may be the same or different, are each a hydrogen atom, a straight or branched alkyl radical having from 1 to 4 carbon atoms, such as methyl, ethyl, n-propyl, isopropyl, n-butyl and isobutyl radicals, a straight or branched alkoxy radical having from 1 to 4 carbon atoms, such as methoxy or ethoxy radicals, a —CHO group, or a chlorine atom, and x is preferably equal to 0 or 1.

Thus, illustrative compounds of formula (I) are:

(1) those of formula (I), in which x is equal to 0, such as phenol;

(2) those of formula (I), in which x is equal to 1, such as:

Pyrocatechol,
Resorcinol,
o-Cresol,
m-Cresol,
2-Ethyl phenol,
3-Ethyl phenol,
2-Propyl phenol,
2-Sec. butyl phenol,
2-Tert. butyl phenol,
3-Tert. butyl phenol,
2-Methoxyphenol (quaiacol),
3-Methoxyphenol,
2-Ethoxyphenol (guaiethol),
Salicylic aldehyde,
Methyl salicylate,
2-Chlorophenol,
3-Chlorophenol,
3-Nitrophenol;

(3) those of formula (I), in which x is equal to 2, such as:

2,3-Dimethyl phenol,
2,5-Dimethyl phenol,
3,5-Dimethyl phenol,
2-Hydroxy 5-acetamidobenzaldehyde,
2-Hydroxy 5-ethamidobenzaldehyde,
2,3-Dichlorophenol,
2,5-Dichlorophenol,
3,5-Dichlorophenol,
Pyrogallol;

(4) those of formula (I), in which x is equal to 3, such as:

2,3,5-Trimethyl phenol,
3,5-Ditert. butyl phenol,
2,3,5-Trichloro phenol;

(5) those of formula (I) having a naphthalene nucleus, such as:

1-Naphthol,
2-Naphthol,
1,2-Dihydroxynaphthalene,
1,5-Dihydroxynaphthalene,
2,3-Dihydroxynaphthalene,
2,6-Dihydroxynaphthalene,
2,7-Dihydroxynaphthalene,
6-Bromo-2-naphthol;

(6) those of formula (I) comprising a plurality of benzene nuclei, such as:

2 -Phenoxypheno l,
3 -Phenoxyphenol.

The preferred aromatic compounds substituted by at least one hydroxyl group are phenol, o-cresol, m-cresol, 3-ethyl phenol, 2-tert. butyl phenol, guaiacol, guaiethol and 2-isopropoxyphenol.

According to the present invention, the condensation of the hydroxylated aromatic compound of formula (I) with the carbonyl compound of formula (II) is carried out in the presence of a quaternary ammonium hydroxide.

The preferred such quaternary ammonium hydroxides are those having the following formula (III):

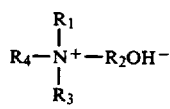

(III)

in which the radicals $R_1$, $R_2$, $R_3$ and $R_4$, which may be the same or different, are each an optionally substituted, straight or branched, alkyl radical having from 1 to 20 and preferably from 1 to 12 carbon atoms, an optionally substituted, aryl radical having from 6 to 12 and preferably from 6 to 10 carbon atoms, an optionally substituted aralkyl radical having from 7 to 14 and preferably from 7 to 10 carbon atoms, with the proviso that two of said radicals $R_1$ to $R_4$ may together form a straight or branched, alkylene radical having from 3 to 6 carbon atoms.

In formula (III), the radicals $R1$, $R2$, $R_3$ and $R_4$ can be an alkyl radical, the hydrocarbon chain of which can be interrupted by a heteroatom, such as, in particular, oxygen or nitrogen, and/or be substituted by substituents, such as, in particular, phenyl, hydroxyl, halogen, nitro, alkoxy or alkoxycarbonyl having from 1 to 6 carbon atoms, and the like.

In the event that the radicals $R_1$, $R_2$, $R_3$ and $R_4$ comprise a cyclic ring member and, in particular, benzene, such ring member can also be substituted, for example by those substituents indicated above.

The radicals $R_1$, $R_2$, $R_3$ and $R_4$ are preferably alkyl radicals having from 1 to 6 carbon atoms, notably methyl, ethyl or butyl; or are phenyl or benzyl radicals.

Exemplary of the preferred quaternary ammonium hydroxides of formula (III) are tetraalkyl ammonium or trialkyl benzyl ammonium hydroxides, the identical or different alkyl radicals of which being straight or branched alkyl radicals having from 1 to 12 and preferably from 1 to 6 carbon atoms.

More preferred are tetramethyl ammonium hydroxide, tetraethyl ammonium hydroxide, and tetrabutyl ammonium hydroxide.

The trialkyl benzyl ammonium hydroxides can also be used, in particular trimethyl benzyl ammonium hydroxide.

In respect of the concentrations and amounts of reagents used, the preferred conditions are indicated below.

According to the present invention a solution of a carbonyl compound of formula (II) is employed. The concentration of said solution is not critical and can vary widely, e.g., from 15% to 100% by weight. Preferably, when using glyoxylic acid as the carbonyl compound of formula (II), a commercial glyoxylic acid solution is used, having a concentration of approximately 50%.

Also according to this invention, the carbonyl compound of formula (II) is reacted with the hydroxylated aromatic compound of formula (I) o The molar ratio between the hydroxylated aromatic compound of formula (I) and the carbonyl compound of formula (II) ranges from 0.3 to 4.0 and preferably from 0.5 to 2.0.

The quaternary ammonium hydroxide solution has a concentration generally ranging from 10% to 50% by weight. The concentration of the starting solution is not critical. However, as the concentration of the hydroxylated aromatic compound of formula (I) is advantageously low in the reaction medium, a dilute solution of quaternary ammonium hydroxide is used to effect the dilution of the reaction medium.

The concentration of the hydroxylated aromatic compound of formula (I) preferably ranges from 0.5 to 1.5 mole/liter and, more particularly, is approximately 1 mole/liter.

The amount of quaternary ammonium hydroxide introduced into the reaction medium takes account of the amount required for salifying all of the salifiable groups of the hydroxylated aromatic compound of formula (I) and the carbonyl compound of formula (II), which can be hydroxyl groups and/or COOH carboxylic functions.

The amount of quaternary ammonium hydroxide can vary widely, and for example can be qual to or close to stoichiometry, or in excess thereof. Generally, the amount of quaternary ammonium hydroxide ranges from 80% to 120% of the stoichiometric amount. The reaction temperature advantageously ranges from 20° to 60° C. and preferably from 30° to 40° C.

The process according to the invention is advantageously carried out at atmospheric pressure, but under a controlled atmosphere of inert gases, preferably nitrogen or rare gases and, in particular, nitrogen.

A preferred embodiment of the invention is set forth below:

Into a reaction medium incorporating the hydroxylated aromatic compound of formula (I), water and quaternary ammonium hydroxide in the necessary amount for salifying the hydroxyl group and other salifiable functions, is introduced the solution of the carbonyl compound of formula (II) and, in parallel, the quaternary ammonium hydroxide solution, in amount necessary for salifying the possible salifiable functions.

If the hydroxylated aromatic compound of formula (I) and the carbonyl compound of formula (II) have salifiable functions, quaternary ammonium hydroxide is also introduced, in an amount necessary for salifying all the salifiable functions.

Stirring of the reaction medium is maintained at a temperature within the above range for period of time having from 1 to 10 hours. At the end of the reaction, the hydroxylated and para-hydroxyalkylated compound obtained is separated in salified form in accordance with conventional procedures.

In the particular case of p-hydroxymandelic acid or 3-methoxy-p-hydroxymandelic acid, these are obtained in salified form and can be separated according to standard separation procedures, particularly crystallization.

The process according to the invention produces hydroxylated and p-hydroxyalkylated aromatic compounds.

In particular, in a preferred embodiment, the process of the invention comprises reacting a hydroxylated aromatic compound according to formula (I) with glyoxylic acid to provide optionally substituted, p-hydroxymandelic compound, which can be represented by the following formula (IV):

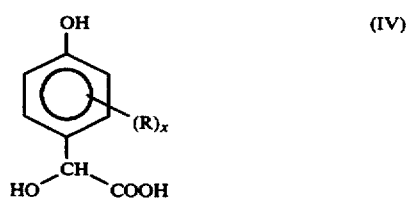

(IV)

in which R and x have the definitions given in respect of the compounds of formula (I).

These compounds are of particular value because they are intermediates, inter alia, for preparing hydroxyaryl acetic acids by reduction, or by oxidation, hydroxyaryl glyoxylic acids (=hydroxyaryl α-oxyacetic acids) or hydroxyaromatic aldehydes.

In a preferred embodiment of the invention, hydroxyaromatic aldehydes are prepared by oxidation of compounds of formula (IV).

The oxidation of the compounds of formula (IV) can be carried out in accordance with the procedures described in the literature. Compare, for example, P. Hebert, *Bull. Soc. Chim. France*, 27, pp. 45–55 (1920) and Nagai Shigeki et al, JP-A-76/128,934. Oxidation is generally carried out by oxygen or air under pressure, in the presence of an appropriate catalyst such as, e.g., derivatives of chromium, cobalt, copper, vanadium or osmium.

Thus, the present invention is especially well suited for the preparation of, e.g., 4-hydroxybenzaldehyde and vanillin and its analogs, for example 3-ethylvanillin, 3-isopropylvanillin, by oxidation, respectively, of p-hydroxymandelic acid and 3-methoxy p-hydroxymandelic or 3-ethoxy p-hydroxymandelic or 3-isopropoxy p-hydroxymandelic acids.

In order to further illustrate the present invention and the advantages thereof, the following specific examples are given, it being understood that same are intended only as illustrative and in nowise limitative.

In said examples to follow, the percentages given are by weight.

The abbreviations employed in said examples have the following definitions:

$$\text{Conversion } (TT) = \frac{\text{number of moles of guaiacol transformed}}{\text{number of moles of guaiacol introduced}}$$

$$\text{Selectivity } (RT) = \frac{\text{number of moles of mandelic acid formed}}{\text{number of moles of guaiacol transformed}}$$

EXAMPLE 1

Into a 1 liter glass reactor equipped with a double envelope, a pH electrode, a temperature sensor, a condenser, an inert gas inlet and a mechanical stirrer were introduced 310 g of distilled water, 138 g (0.281 mole) of an aqueous 30% quaternary tetraethyl ammonium hydroxide solution and 69.7 g (0.56 mole) of guaiacol.

An inert atmosphere was established and the reaction mixture was heated to 35° C., while simultaneously adding, over two hours, 138 g (0.281 mole) of said aqueous 30% quaternary ammonium hydroxide solution and 41.6 g of an aqueous 50% glyoxylic acid solution. The reaction mixture was maintained for 2 hours at 35° C. At the end of the reaction, the products of the reaction were determined by high performance liquid chromatography.

The following results were obtained:
Conversion: TT=44.0%,
4-Hydroxy-3-methoxymandelic acid: RT=97%,
2-Hydroxy-3-methoxymandelic acid: RT=2.7%,
2-Hydroxy-3-methoxy-1,5-dimandelic acid: RT=1.1%.

COMPARATIVE EXAMPLE 2

The procedure of Example 1 was repeated except that soda was introduced instead of tetraethyl ammonium hydroxide. The following results were obtained:
Conversion: TT=43%,
4-Hydroxy-3-methoxymandelic acid: RT=88%,
2-Hydroxy-3-methoxymandelic acid: RT=4.5%,
2-Hydroxy-3-methoxy-1,5-dimandelic acid: RT=6.9%.

COMPARATIVE EXAMPLES 3 and 4 and EXAMPLES 5 to 8

In these examples, the procedure of Example 1 was repeated, except that all of the reagents were introduced simultaneously and the reaction medium was maintained at 35° C. for 3 hours.

Examples 3 and 4 are comparative tests, where the alkyl ammonium hydroxide was replaced by soda or ammonia.

The results obtained are reported in the following Table:

TABLE

| Example | Quaternary ammonium hydroxide | TT | RT para | RT ortho | RT di |
|---|---|---|---|---|---|
| 3 | soda (comparative) | 42.0 | 60.0 | 4.3 | 2.2 |
| 4 | ammonia (comparative) | 51.0 | 0 | 0 | 2.5 |
| 5 | tetramethyl ammonium hydroxide | 38.5 | 96.0 | 2.7 | 1.0 |
| 6 | tetrapropyl ammonium hydroxide | 40 | 95.6 | 3.3 | 1.1 |
| 7 | tetrabutyl ammonium hydroxide | 32.0 | 63.5 | 2.0 | 0.7 |
| 8 | trimethyl benzyl ammonium hydroxide | 33.0 | 95.0 | 3.9 | 1.0 |

In the above table, the abbreviations ortho, para and di connote:
4-hydroxy-3-methoxymandelic acid=para
2-hydroxy-3-methoxymandelic acid=ortho
2-hydroxy-3-methoxy-1,5-dimandelic acid=di.

From the Table, it will be seen that the use of a quaternary ammonium hydroxide permits improving the selectivity of the reaction.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the para-hydroxyalkylation of a hydroxylated aromatic compound unsubstituted in the para-position to the hydroxy group thereof, comprising condensing such hydroxylated aromatic compound with an organic carbonyl compound in the presence of a quaternary ammonium hydroxide and forming a para-hydroxyalkylated aromatic compound.

2. The process as defined by claim 1, said hydroxylated aromatic compound having the formula (I):

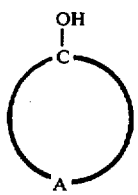

in which A is the residue of an aromatic or carbocyclic, mono- or polycyclic ring member having at least 5 atoms, and said carbonyl compound having the formula (II):

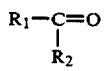

in which $R_1$ is a hydrogen atom, a straight or branched alkyl radical having from 1 to 6 carbon atoms, or a phenyl radical, and $R_2$ is an electron-attracting group.

3. The process as defined by claim 2, said hydroxylated aromatic compound having the formula (I):

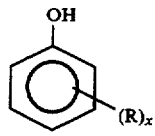

in which the position para to the hydroxyl group is unsubstituted; x is an integer ranging from 1 to 4; and R is a hydrogen atom, an alkyl, alkoxy, hydroxyalkyl, cycloalkyl, aryl, phenoxy, alkoxyalkyl, fluoroalkyl or hydroxyalkoxyalkylene radical having from 1 to 20 carbon atoms, a hydroxyl group, a —CHO group, an acyl radical having from 2 to 6 carbon atoms, or a halogen atom, with the proviso that two radicals R depending from adjacent carbon atoms may together form, with said adjacent carbon atoms, a benzene nucleus.

4. The process as defined by claim 3, wherein said hydroxylated aromatic compound of formula (I), x is equal to 0, 1, 2 or 3; and R is a hydrogen atom, a straight or branched alkyl radical having from 1 to 10 carbon atoms, a straight or branched alkoxy radical having from 1 to 10 carbon atoms, a —OH group, a —CHO group, a halogen atom, or a —CF$_3$ group.

5. The process as defined by claim 4, wherein said hydroxylated aromatic compound of formula (I), the radicals R, which may be identical or different, are each a hydrogen atom, a straight or branched alkyl radical having from 1 to 4 carbon atoms, a straight or branched alkoxy radical having from 1 to 4 carbon atoms, a —CHO group, or a chlorine atom, and x is equal to 0 or 1.

6. The process as defined by claim 2, said hydroxylated aromatic compound comprising phenol, o-cresol, m-cresol, 3-ethylphenol, 2-tert. butylphenol, guaiacol, guaiethol or 2-isopropoxyphenol.

7. The process as defined by claim 2, wherein said carbonyl compound of formula (II), $R_2$ is a —CHO group, or an $R_3$—CO— or $R_3$—CO—(CH$_2$)$_m$ radical, in which $R_3$ is a straight or branched alkyl radical having from 1 to 6 carbon atoms and m a number ranging from 1 to 3, a —COOR$_4$ radical, in which $R_4$ is a hydrogen atom or a straight or branched alkyl radical having from 1 to 6 carbon atoms, a —CX$_2$H group, in which X is a halogen atom, or a —CX$_3$ group, in which X is a halogen atom.

8. The process as defined by claim 2, said carbonyl compound of formula (II) comprising glyoxal, glyoxylic acid, chloral, bromal, fluoral, dichloroacetone, trifluoroacetone, trifluoroacetophenone, trifluoroacetylacetone, methyl pyruvate or ethyl pyruvate.

9. The process as defined by claim 1, said quaternary ammonium hydroxide having the formula (III):

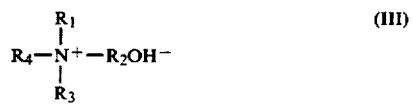

in which the radicals $R_1$, $R_2$, $R_3$ and $R_4$, which may be the same or different, are each a straight or branched, optionally substituted alkyl radical having from 1 to 20 carbon atoms, an optionally substituted aryl radical having from 6 to 12 carbon atoms, or an optionally substituted aralkyl radical having from 7 to 14 carbon atoms, with the proviso that two of said radicals $R_1$ to $R_4$ may together form a straight or branched alkylene radical having from 3 to 6 carbon atoms.

10. The process as defined by claim 9, said quaternary ammonium hydroxide comprising a tetraalkyl ammonium hydroxide or a trialkyl benzyl ammonium hydroxide, the alkyl moieties of which, which may be the same or different, are straight or branched alkyl radicals having from 1 to 12 carbon atoms.

11. The process as defined by claim 9, said quaternary ammonium hydroxide comprising tetramethyl ammonium hydroxide, tetraethyl ammonium hydroxide, tetrabutyl ammonium hydroxide or trimethyl benzyl ammonium hydroxide.

12. The process as defined by claim 1, said carbonyl compound comprising an aqueous solution thereof, at a concentration ranging from 15% to 100% by weight.

13. The process as defined by claim 1, wherein the molar ratio between the hydroxylated aromatic compound and the carbonyl compound ranges from 0.3 to 4.0.

14. The process as defined by claim 1, said quaternary ammonium hydroxide comprising an aqueous solution thereof, at a concentration ranging from 10% to 50% by weight.

15. The process as defined by claim 1, wherein the amount of said quaternary ammonium hydroxide ranges from 80% to 120% of the stoichiometric amount required to salify all salifiable groups of said hydroxylated aromatic compound and of said carbonyl compound.

16. The process as defined by claim 1, wherein the concentration of said hydroxylated aromatic compound in the medium of reaction ranges from 0.5 to 1.5 mole/liter.

17. The process as defined by claim 1, carried out at a reaction temperature ranging from 20° to 60° C.

18. The process as defined by claim 1, comprising preparing 3-methoxy-p-hydroxymandelic acid by condensing guaiacol and glyoxylic acid, in water, and in the presence of said quaternary ammonium hydroxide.

19. The process as defined by claim 1, further comprising converting the product thereof into a hydroxy aryl acetic acid, a hydroxy aryl glyoxylic acid, or a hydroxy aromatic aldehyde.

20. The process as defined by claim 1, further comprising oxidizing the product thereof into 4-hydroxybenzaldehyde, vanillin or analog thereof.

* * * * *